United States Patent [19]
Glahn

[11] Patent Number: 6,017,713
[45] Date of Patent: Jan. 25, 2000

[54] FERRITIN FORMATION AS AN PREDICTOR OF IRON AVAILABILITY IN FOODS

[75] Inventor: Raymond P Glahn, Ithaca, N.Y.

[73] Assignee: The United States of America, as represented by the Secretary of Agriculture, Washington, D.C.

[21] Appl. No.: 09/266,950

[22] Filed: Mar. 12, 1999

[51] Int. Cl.$^7$ ........................................................ C12Q 1/68
[52] U.S. Cl. ................................................ 435/6; 435/371
[58] Field of Search ................................. 435/6, 325, 371

[56] References Cited

PUBLICATIONS

Glahn et al., *Journal of the Federation of American Societies for Experimental Biology*, Abstracts Part II, No. 4134, vol. 8(5), Mar. 18, 1994.

R.P. Glahn, *Journal of the Federation of American Societies for Experimental Biology*, Abstracts Part II, No.'s 5709–5711, vol. 9(4), Mar. 10, 1995.

R.P. Glahn, *Journal of the Federation of American Societies for Experimental Biology*, Abstract No.'s 4892, 4893 & 4908, vol. 12(2), 1998.

Glahn et al., *American Institute of Nutrition*, pp. 330–339, 1996.

Glahn et al., *American Society of Nutritional Sciences*, pp. 257–264, 1998.

Glahn et al., *American Society of Nutrition Sciences*, pp. 1555–1561, 1998.

Gangloff et al., *American Institute of Nutrition*, pp. 3118–3127, 1996.

Gangloff et al., *American Institute of Nutrition*, pp. 3118–3127, 1996.

Alvarez–Hernandez et al., *American Institute of Nutrition*, pp. 1574–1580, 1994.

*Primary Examiner*—James Ketter
*Attorney, Agent, or Firm*—M. Howard Silverstein; John D. Fado; Janelle S. Graeter

[57] ABSTRACT

An in vitro system has been developed capable of effectively predicting the iron (Fe) availability of foods and food products. The system utilizes the formation of ferritin in intestinal epithelial cells as an indicator of Fe uptake from peptic and intestinal food digests.

3 Claims, 15 Drawing Sheets

FERRITIN FORMATION AS AN PREDICTOR OF IRON AVAILABILITY IN FOODS

BACKGROUND OF THE INVENTION

1. Field of the Invention

The invention relates to a method for effectively predicting the availability of iron (Fe) in foods utilizing ferritin formation in intestinal epithelial cells as an indicator.

2. Description of the Relevant Art

An intestinal epithelial cell line is a useful model for studies of iron uptake in humans. The Caco-2 cell line has been described as such a model in a number of studies (e.g. Glahn et al. 1994. FASEB Journal. vol. 8, no. 5, abstr. No. 4134; Wien et al. 1995. FASEB Journal. vol. 9, no. 4, abstr. No. 5711; Glahn et al. 1996. J. Nutr. vol. 126, pp. 332–339; Glahn et al. 1998. J. Nutr. vol. 128, pp. 257–264, all herein incorporated by reference). These applications all required the extrinsic radiolabeling of the food Fe. Intrinsic radiolabeling as a means of tracking Fe absorption for plant foods has also been utilized, however, it is a relatively expensive and time-consuming process which requires a facility and technical staff to support the growth of radiolabeled plant materials. In addition, it may be difficult to incorporate sufficient radioactivity into the food studied, particularly for use in in vitro systems.

Thus, an in vitro model system that does not require radiolabeling of food Fe would be advantageous with respect to both time, cost, reliability and convenience. It would enable the measurement of food Fe availability in foods obtained directly from the producer or the supermarket shelf and would eliminate concerns of adequate radiolabeling of food Fe present in a complete meal.

SUMMARY OF THE INVENTION

I have discovered that an in vitro digestion cell culture model system may be utilized to measure food Fe availability by measuring ferritin formation as an indicator of cell Fe uptake, thus eliminating the need for radiolabeling of food Fe in availability assays.

In accordance with this discovery, it is an object of the invention to provide a novel method for predicting Fe availability in a food sample by measuring ferritin formation by intestinal epithelial cells as an indicator of cell Fe uptake.

Other objects and advantages will become readily apparent from the following description.

DETAILED DESCRIPTION OF THE INVENTION

Figure 1:
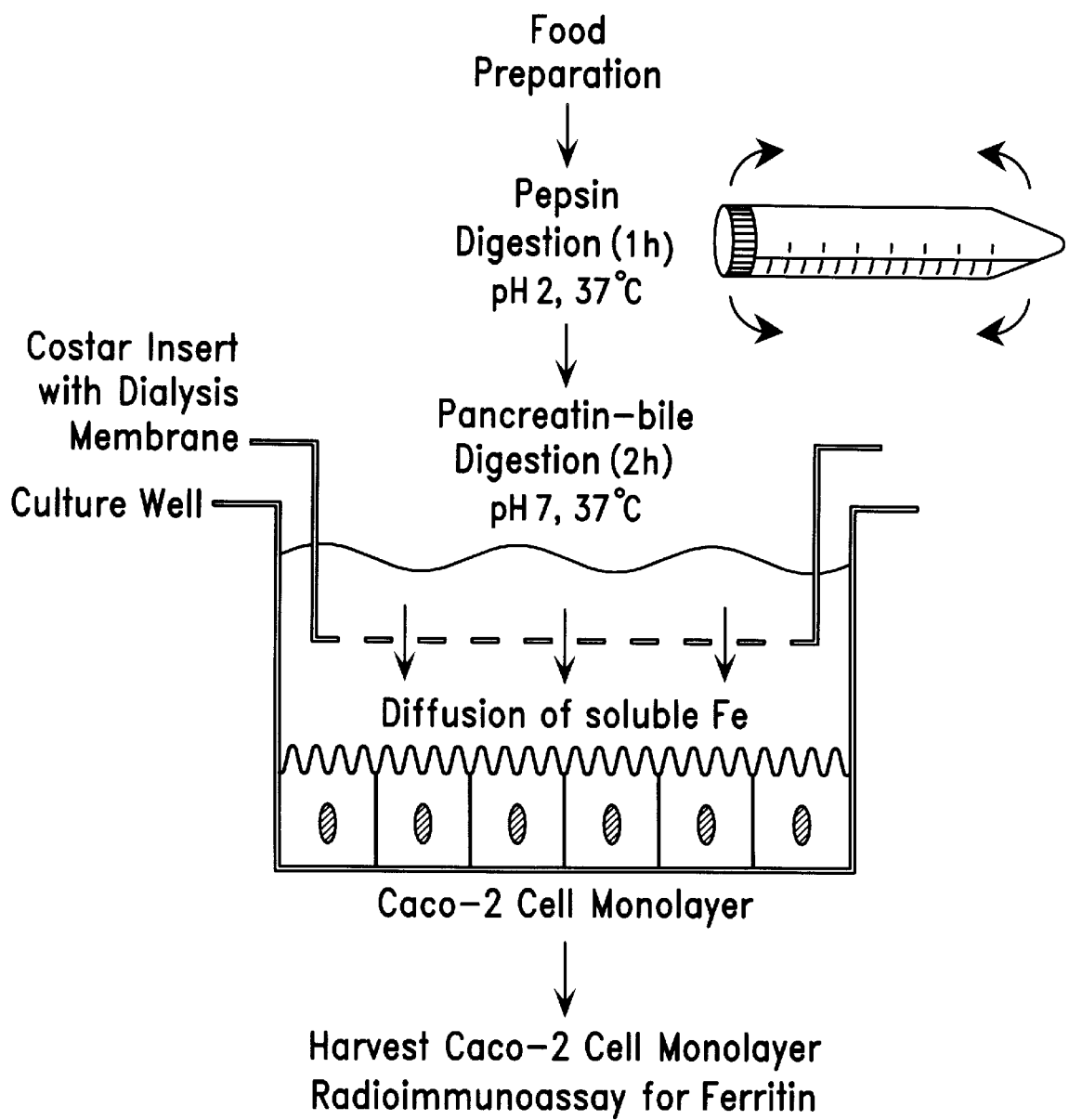
FIG. 1 is a diagram of an in vitro digestion/cell culture model using human intestinal epithelial Caco-2 cells.

An in vitro digestion cell culture model to measure food Fe availability was developed using an intestinal epithelial cell line. The method utilized combines simulated digestion conditions of the human intestinal lumen with uptake of Fe by cultured human intestinal epithelial cells. In order to combine in vitro digestion techniques with epithelial cell cultures, a dual chamber system utilizing a dialysis membrane attached to an insert ring was developed (FIG. 1). The insert ring creates an upper chamber in which to place a food digest while the dialysis membrane protects the cells from digestive enzymes and the aseptic contents of the digest.

In early experiments, Fe uptake was measured using extrinsically added radioactive Fe to the digest. Radioactive Fe associated with the cells was then quantified by gamma counter. In more recent experiments, ferritin, the intracellular storage protein for Fe, was used as a marker for cell Fe uptake, thereby eliminating the need for using radioisotopes to measure Fe uptake and availability. Fe availability can now be measured from food or food ingredients directly from a manufacturer, grower or supermarket shelf without the costs and inconvenience associated with Fe radiolabeling.

The novel method is carried out according to the following steps:

1) preparing a culture of intestinal epithelial cells;
2) preparing an insert comprising a dialysis membrane capable of allowing diffusion of Fe from a digest of a food sample and simultaneously protecting cells from digestive enzymes and microbial contamination present in the digest;
3) preparing a peptic digestion of a food sample, followed by an intestinal digest;
4) preparing a monolayer of intestinal epithelial cells in Fe-free culture medium in a chamber;
5) fitting the insert of step 2) into the chamber of step 4) such that the membrane is secured with a liquid tight seal, resulting in a two-chamber system having a lower chamber with a cell monolayer attached to the bottom surface and an upper chamber formed by the membrane, with the membrane in fluid contact with the culture medium;
6) adding an aliquot of the intestinal digest to the upper chamber and incubating the digest for a predetermined time, allowing diffusion of Fe-containing fluid into the lower chamber as digestion occurs;
7) removing the insert containing the intestinal digest;
8) adding additional Fe-free medium to the lower chamber containing the cell monolayer;
9) incubating the cells for a period of time sufficient for ferritin formation to occur; and
10) harvesting the cells and measuring the amount of ferritin formed.

While any intestinal epithelial cell line is considered useful for carrying out the method depending on the experimental objectives, human cells are preferred for human nutrition studies, and the Caco-2 cell line mentioned supra is particularly preferred. The model conditions have been designed to simulate the gastrointestinal environment and allow uptake to occur simultaneously with food digestion under pH conditions similar to those found along the absorptive surface of the intestinal tract (Berne and Levy. 1993. In: *Physiology*, 3rd ed. Berne, R. M. and Levy, M. N., eds. Mosby-Year Book Inc., St. Louis, Mo., pp. 688–716; Guyton and Hall. 1996. In: *Textbook of Medical Physiology*, 9th ed. Guyton, A. C. and Hall, J. E., eds. W.B. Saunders Company, Philadelphia, Pa., pp. 815–832). The utilization of human-derived cells permits experimentation that might not be feasible or practical in vivo. For example, as a prelude to human trials, it may enable improved design and productivity of the human experiment. Anticipated applications of the model system include food product development such as infant formula and cereals, screening of plant cultivars for improved iron availability, development of improved iron supplements and studies of the precise factors in digests of animal tissue that promote iron uptake.

The particular parameters utilized when carrying out the novel method are not critical so long as the relevant physiological conditions are simulated as closely as possible. These conditions are well-known to those of skill in the art. For example, the pepsin digestion may be carried out at a pH in the range of about 2 to about 4. A pH of about 2 would be preferable for adult human nutrition studies; however, digestion occurs at a higher pH in infants (about 3 to about 4), therefore studies involving infant nutrition should take that difference into consideration.

Another variable is the incubation time for digestion of the test samples. Again, preferably one would mimic physiological conditions as much as reasonably possible. The pepsin digestion may be carried out from about 30 min to about 90 min to produce a sample which can ultimately provide useful results. The intestinal digestion may be carried out from about 1 hr to about 4 hr.

An additional variable is the time period for the incubation of the cell monolayer to allow ferritin formation to occur. Measurable ferritin formation occurs within 2 to 3 hr, especially if there is abundant Fe available in the test sample. It is recommended, however, that in order to obtain more accurate results, cell incubation be carried out for a longer period of time, i.e. up to about 24 hr.

Guidelines for carrying out the novel procedure are presented hereinbelow and in the specific examples. These examples are intended as guidance only and may be varied by those of skill in the art to fit the particular test objectives.

A cell culture was prepared as described in Example 1, using Caco-2 cells (American Type Culture Collection, Rockville, Md.) seeded in collagen-treated 6-well plates (Costar, Cambridge, Mass.). The cells were grown in Dulbecco's modified Eagle's medium (GIBCO, Grand Island, N.Y.) with 10% fetal calf serum (GIBCO, supra), 25 mmol/L HEPES (Sigma Chemical Co., St. Louis, Mo.) and 1% antibiotic antimycotic solution (GIBCO, supra) and incubated at 37° C. under 5% $CO_2$/95% air at constant humidity.

Peptic and intestinal digests were prepared as described in Example 2. Both digestions were carried out on a rocking platform shaker (Reliable Scientific, Hernando, Miss.) in an incubator at 37° C. with a 5% $CO_2$/95% air atmosphere maintained at constant humidity. The peptic digest was carried out at about pH 2 in a culture tube incubated for about 1 hr. The intestinal digestion was carried out at a final pH of about 7 in the upper chamber of the two-chamber system for about 2 hr.

The insert utilized for creating the upper chamber for the intestinal digest was prepared as described in Example 3. A Transwell insert ring sized to fit the cell culture chamber (or well) was fitted with a dialysis membrane (Spectra/Por 2.1, Spectrum Medical, Gardena, Calif.) to form the bottom of the upper chamber, and held in place with a silicone ring (Web Seal, Rochester, N.Y.). The membrane was soaked in deionized water before attachment to the ring, and the entire unit was sterilized and stored in sterile water until used.

The intestinal epithelial monolayer was prepared as described in Example 4, with an aliquot of fresh Fe-free medium covering the cells during the experiment. A sterilized insert was inserted into the well, with the membrane in fluid contact with the culture medium. An aliquot of the intestinal digest was pipetted into the upper chamber, the chamber covered and placed in an incubator. Upon termination of the intestinal digestion, the insert ring and digest were removed, and an additional aliquot of medium was added to that in the well. The culture was incubated for an additional period of time sufficient for ferritin formation to occur, about 22 hr. The cells were then harvested for analysis as described in Example 5. Cellular ferritin content was measured by radioimmunometric assay as described in Example 6.

Experiments were carried out to test the efficacy of the system. Ferritin formation by intestinal epithelial cells occurs in response to Fe that has been taken up but not transported across the basolateral surface (Beard et al. 1996. *Nutr. Rev.* vol. 54, pp. 295–317). Previous studies of the relationship between Fe uptake and Caco-2 cell ferritin content demonstrated an inverse correlation between the rate of Fe uptake and the "Fe status" of the cell monolayer (Alvarez-Hernandez et al. 1991. *Biochim. Biophys. Acta.* vol. 1070, pp. 205–208; Gangloff et al. 1996. *J. Nutr.* vol. 126, pp. 3118–3127), i.e. Caco-2 cell monolayers cultured in low Fe-containing media exhibited low ferritin content and a high rate of iron uptake. Conversely cells cultured in high Fe media exhibited high ferritin content and a lower rate of Fe uptake. These studies clearly demonstrated that Caco-2 cells synthesize ferritin in response to Fe uptake in proportion to the Fe content of the culture medium.

The culture conditions used in these experiments were designed to generate cells of relatively low Fe status. The culture media contained low amounts of available Fe; therefore the cells formed minimal amounts of ferritin and exhibited near maximal rates of Fe uptake. Iron uptake and ferritin content of cells cultured under these conditions have been previously characterized (Gangloff et al., supra). It was necessary to establish these conditions in order to adequately determine that ferritin formation could serve as a measure of Fe uptake and availability. These conditions thus allow for maximal sensitivity of the system to detect differences in food Fe availability.

Ascorbic acid has long been known to be a strong enhancer of iron uptake and availability. It was therefore used to test for a positive relationship between ferritin formation and Fe uptake, and experiments were designed to determine if ferritin formation by Caco-2 cells over a 24-hr period was proportional to cell iron uptake. Varying amounts of Fe in the form of $FeSO_4$ were added to the digest with excess ascorbic acid (1 mmol/L). Under these conditions, Fe added as $FeSO_4$ in the presence of excess ascorbic acid should be highly available and should result in higher ferritin formation.

FIG. 2 shows the effect of increasing Fe in the digest (in the presence of 1 mmol/L ascorbic acid) on ferritin formation by Caco-2 cell monolayers. Digests contained 0, 10, 20, 50 and 100 $\mu$mol/L Fe added as $FeSO_4$. An additional digest containing only 1 mmol/L ascorbic acid was added as a control to monitor the promotional effect of the ascorbic acid on trace amounts of Fe contributed from the digestive enzymes and system components. A blank was also included which contained the digest components only (pepsin, pancreatin, bile salt) with no added $FeSO_4$ or ascorbic acid. FIG. 2A represents the total Fe measured in a 1.5-mL aliquot of the digest that was placed in the upper chamber at the start of the intestinal digestion period. The amount of Fe measured was consistent with the expected Fe content of the digest. Increasing amounts of Fe in the digest resulted in corresponding increases in the amount of Fe that diffused into the bottom chamber (FIG. 2B). FIG. 2C represents the amount of Fe present in the bottom chamber solution 24 hr after the start of the intestinal digestion period. For this measurement, the digest formulated to contain 100 $\mu$mol/L Fe was significantly greater than the other digests, all of which exhibited Fe concentration similar to that of the blank digest. Presumably, the cells took up most of the Fe that diffused into the bottom chamber with the exception of the treatment containing 100 $\mu$mmol/L Fe. FIG. 2D illustrates the Fe associated with the cell monolayer as measured by inductively coupled plasma (ICP) emission spectroanalysis. Caco-2 cell Fe content corresponded to increased amount of Fe in the digest. Ferritin formation increased with increasing digest Fe concentration (FIG. 2E). The digest containing only ascorbic acid and no added Fe exhibited a significant increase in ferritin formation relative to the blank digest, but was significantly less than that of the digest containing 10 $\mu$mol/L Fe. Of interest is the lack of a significant difference in ferritin formation between the digests containing 50 and 100 $\mu$mol/L Fe. Plotting cell Fe content vs. cell ferritin formation resulted in a nonlinear correlation as shown in FIG. 2F.

Figure 2A:
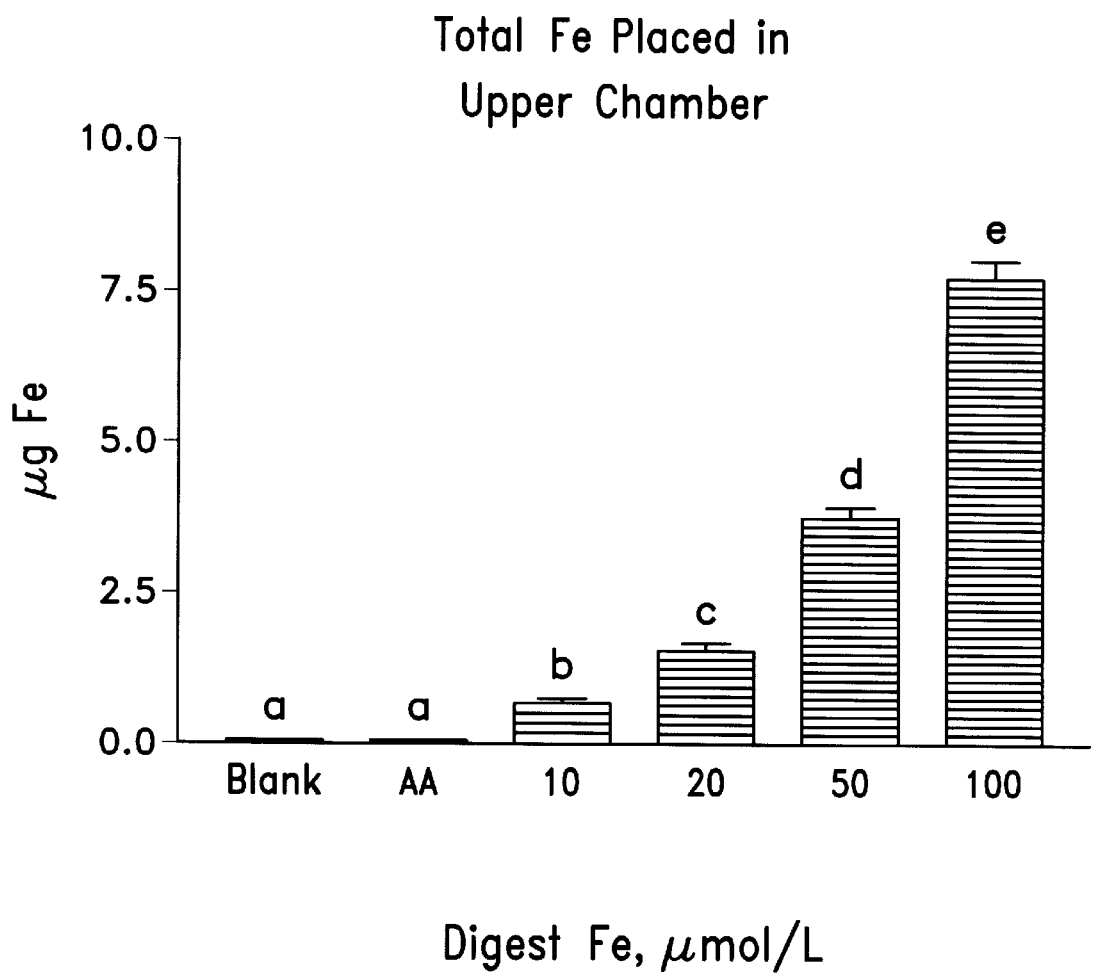
FIGS. 2a–2f shows the measured variables for experiments comparing digests containing $FeSO_4$ and (0–100 $\mu$mol/L) combined with ascorbic acid (AA) at a concentration of 1 mmol/L. Digest concentrations of $FeSO_4$ and AA represent values calculated from the formulation at the start of the intestinal digestion period. "Blank" indicates digest system components only (i.e. pepsin, pancreatin, bile extract), no added $FeSO_4$ or AA. Bars (mean ±SEM, n=5) with no letters in common are significantly different (P<0.05). Specific panels are defined as follows: (A) total amount of Fe measured in 1.5 mL of digest placed in the upper chamber at the start of the intestinal digestion period; (B) amount of Fe measured in the bottom chamber of plates having no cells present immediately after the 2-hr intestinal digestion period; (C) amount of Fe measured in the bottom chamber of wells with cells present. Samples collected 24 hr after the start of the intestinal digestion period; (D) Caco-2 cell Fe content after harvest of the cells 24 hr after the start of the intestinal digestion period; (E) Caco-2 cell ferritin formation as measured 24 hr after the start of the intestinal digestion period; (F) plot of cell Fe content vs. cell ferritin measured 24 hr after the start of the intestinal digestion period. Pearson r=0.91.
Figure 2B:
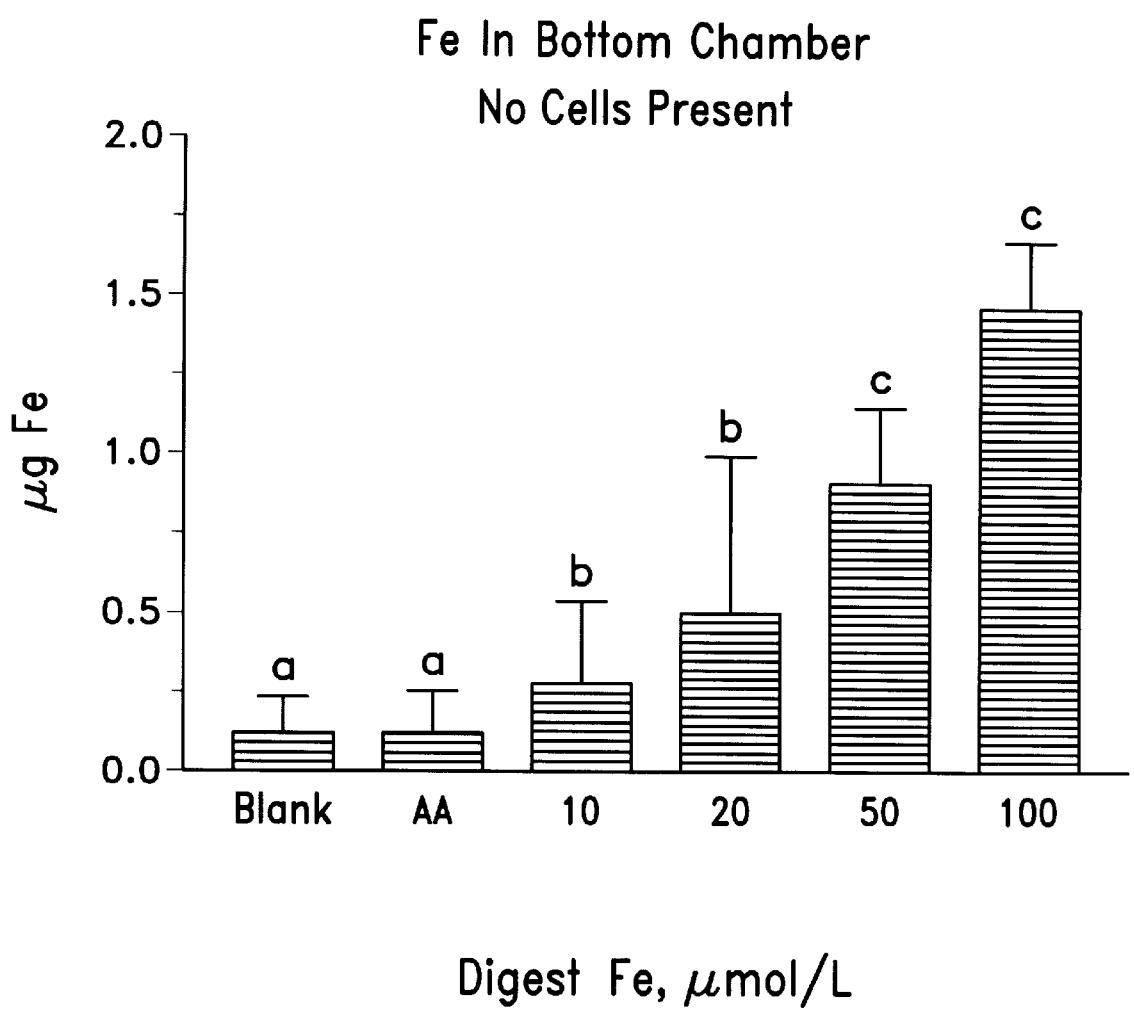
Figure 2C:
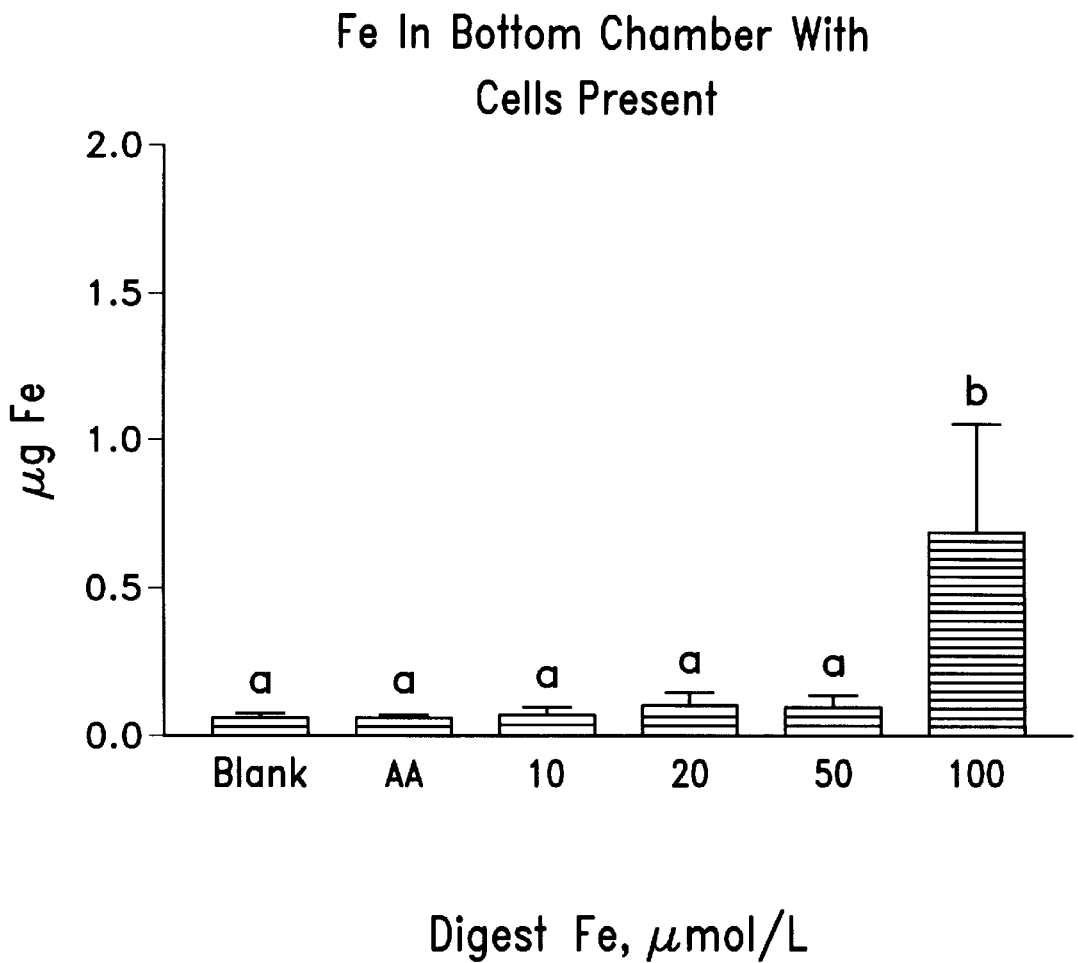
Figure 2D:
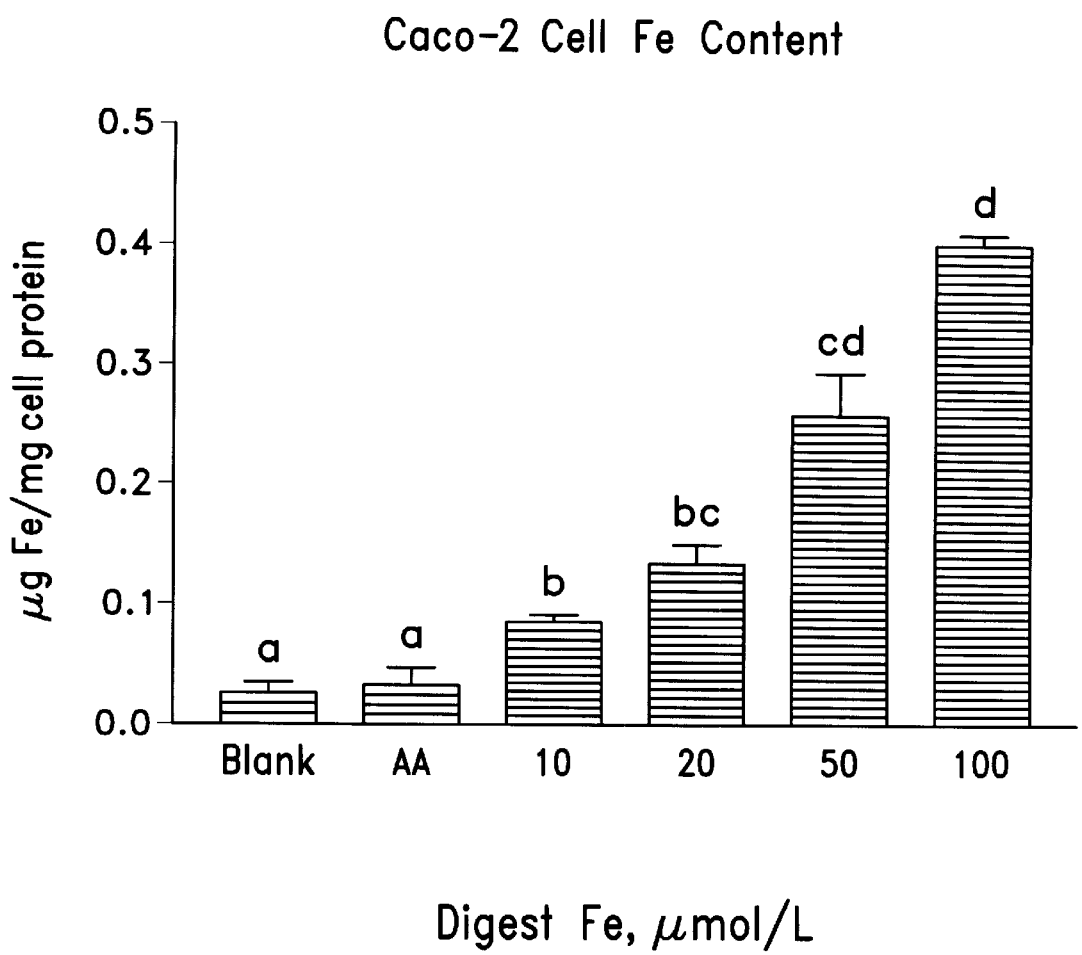

The results shown in FIG. 2 thus clearly demonstrate an increase in ferritin formation associated with the amount of Fe placed in the upper chamber (FIG. 2A) or that which diffused into the bottom chamber (FIG. 2B). The results shown in FIGS. 2C and 2D indicate that much of the Fe that diffused into the bottom chamber was taken up by the cell monolayer. Because ferritin formation is positively associated with cell Fe content (FIGS. 2D, E and F), the results demonstrate that ferritin formation is representative of cell Fe uptake.

The results of FIG. 2 also indicate that maximal Fe uptake from these conditions may occur with between 50 and 100 $\mu$mol/L Fe in the digest. For example, in the presence of cells, the digest containing 100 $\mu$mol/L Fe was the only digest that exhibited values greater than the blank control digest for the amount of bottom chamber Fe (FIG. 2C). The amount of ferritin formation also supports this conclusion because ferritin values were not different between the 50 and 100 $\mu$mol/L digests (FIG. 2E).

Figure 3A:
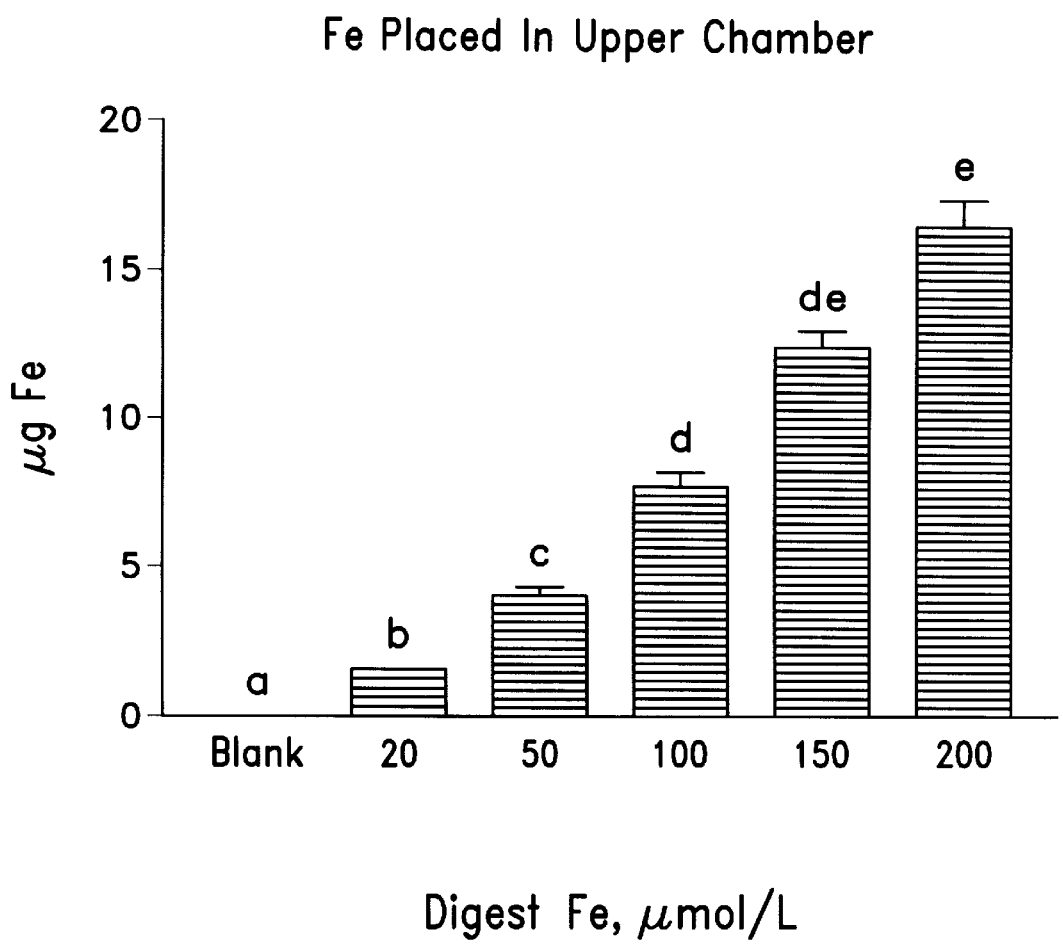
FIG. 3a–3d show the measured variables for experiments comparing digests containing $FeSO_4$ (0–200 $\mu$mol/L) combined with citric acid at a 2:1 molar ratio of citric acid to Fe. Digest concentrations of $FeSO_4$ and citric acid represent values calculated from the formulation at the start of the intestinal digestion period. "Blank" indicates digest system components only (i.e. pepsin, pancreatin, bile extract), no added Fe or citric acid. Bars (mean±SEM, n=4) with no letters in common are significantly different (P<0.05). Specific panels are defined as follows (A) amount of Fe measured in 1.5 mL of digest placed in the upper chamber at the start of the intestinal digestion period; (B) amount of Fe measured in the bottom chamber of plates having no cells present 2 hr after the start of the intestinal digestion period; (C) Caco-2 cell ferritin formation as measured 24 hr after the start of the intestinal digestion period; (D) plot of cell Fe content vs. cell ferritin as measured 24 hr after the start of the intestinal digestion period. Pearson r=0.93.
Figure 3B:
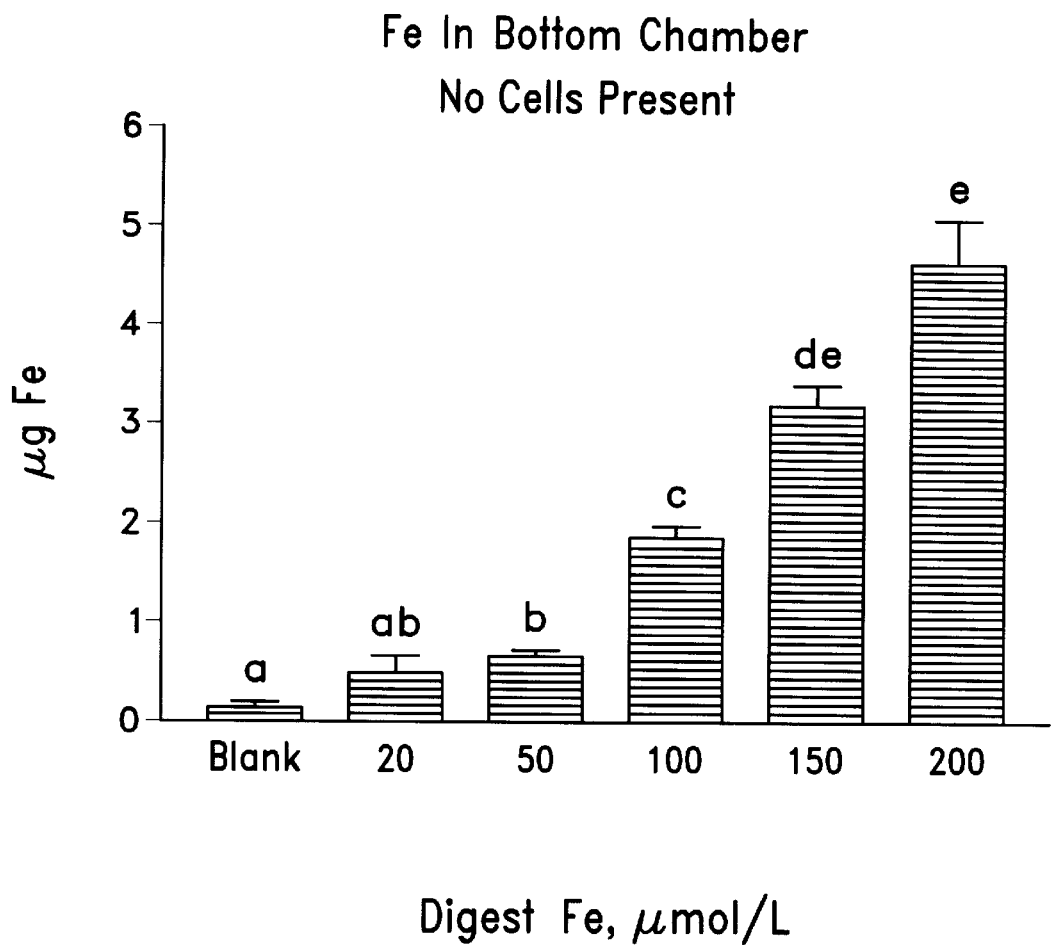

To further test the relationship between ferritin formation and Caco-2 cell Fe uptake, $FeSO_4$ in the presence of citric acid was added at varying concentrations (20–200 $\mu$mol/L) to the digests. Like most ferric iron chelates, citric acid has been shown to keep Fe soluble yet in a less available form than Fe in the presence of ascorbic acid (Alvarez-Hernandez et al., supra). It was therefore expected that Fe uptake from these digests and the subsequent ferritin formation would be less than that of the Fe-ascorbate digests. Ferritin formation from cells exposed to digests containing $FeSO_4$ in the presence of citric acid at a 2:1 molar ratio of citrate to Fe is summarized in FIG. 3. The amount of Fe placed in the upper chamber increased proportionately with the calculated Fe concentration of the digest, as expected (FIG. 3A). Relative to the blank digest, the amount of Fe that diffused into the bottom chamber of plates with no cells present increased proportionately for digest Fe concentrations $\leq 50$ $\mu$mol/L (FIG. 3B). Caco-2 cell ferritin formation exhibited a relatively linear relationship (FIG. 3D).

Figure 2E:
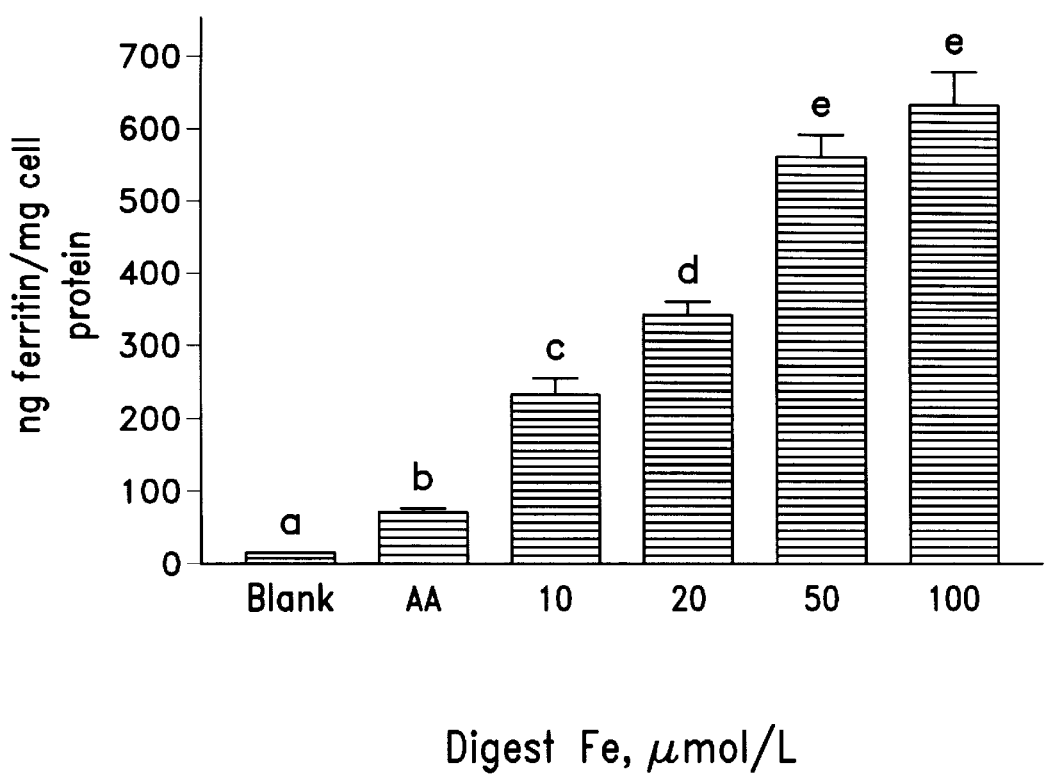
Figure 2F:
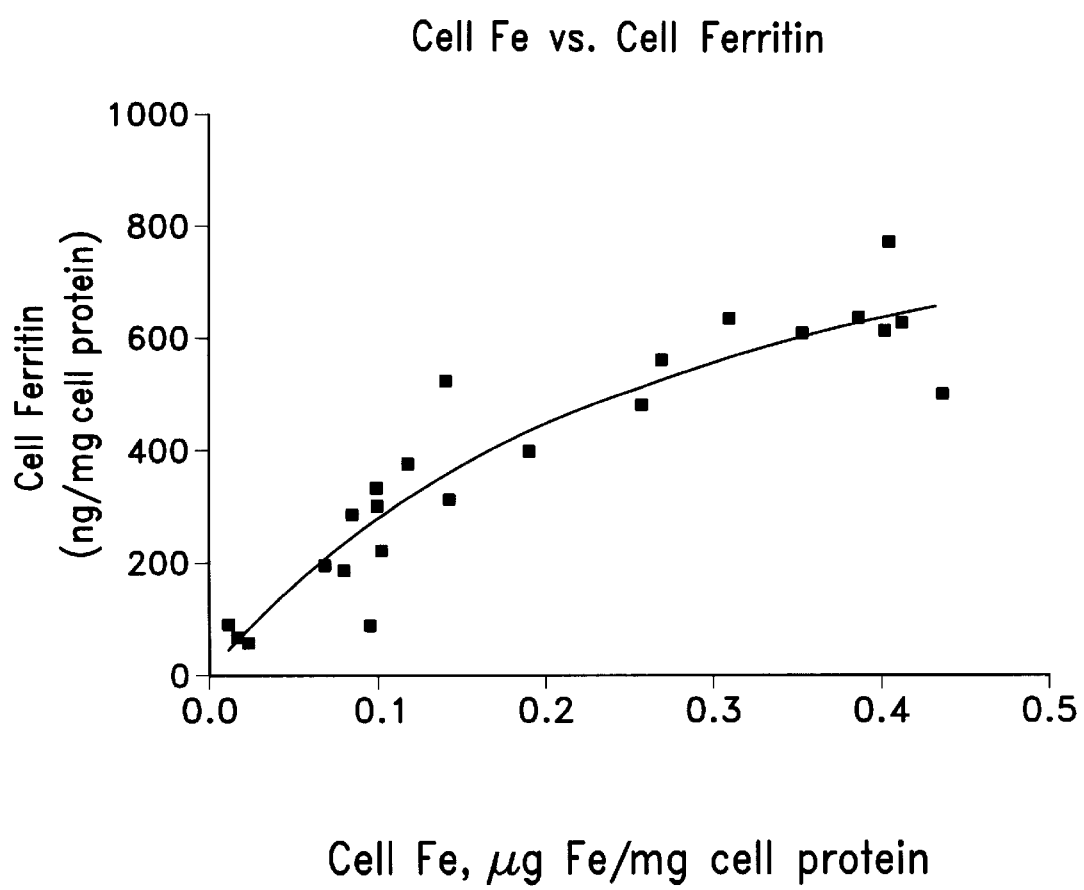
Figure 3C:
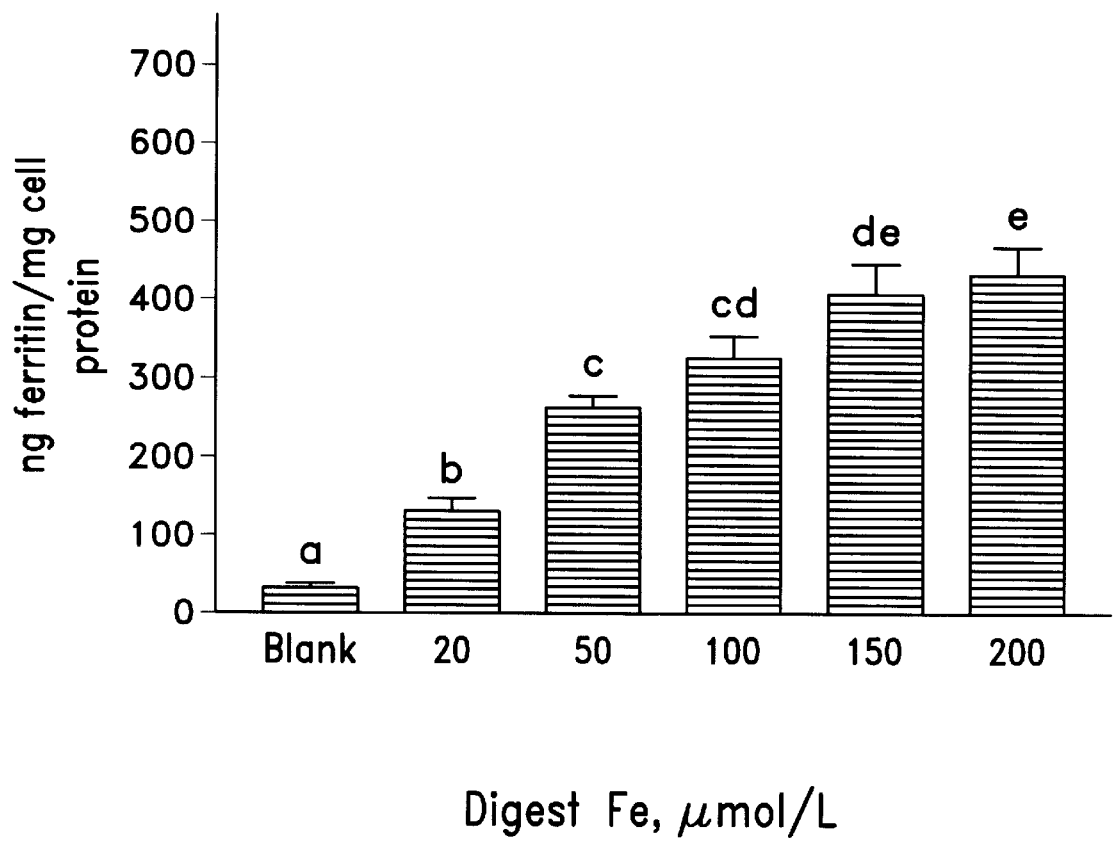
Figure 3D:
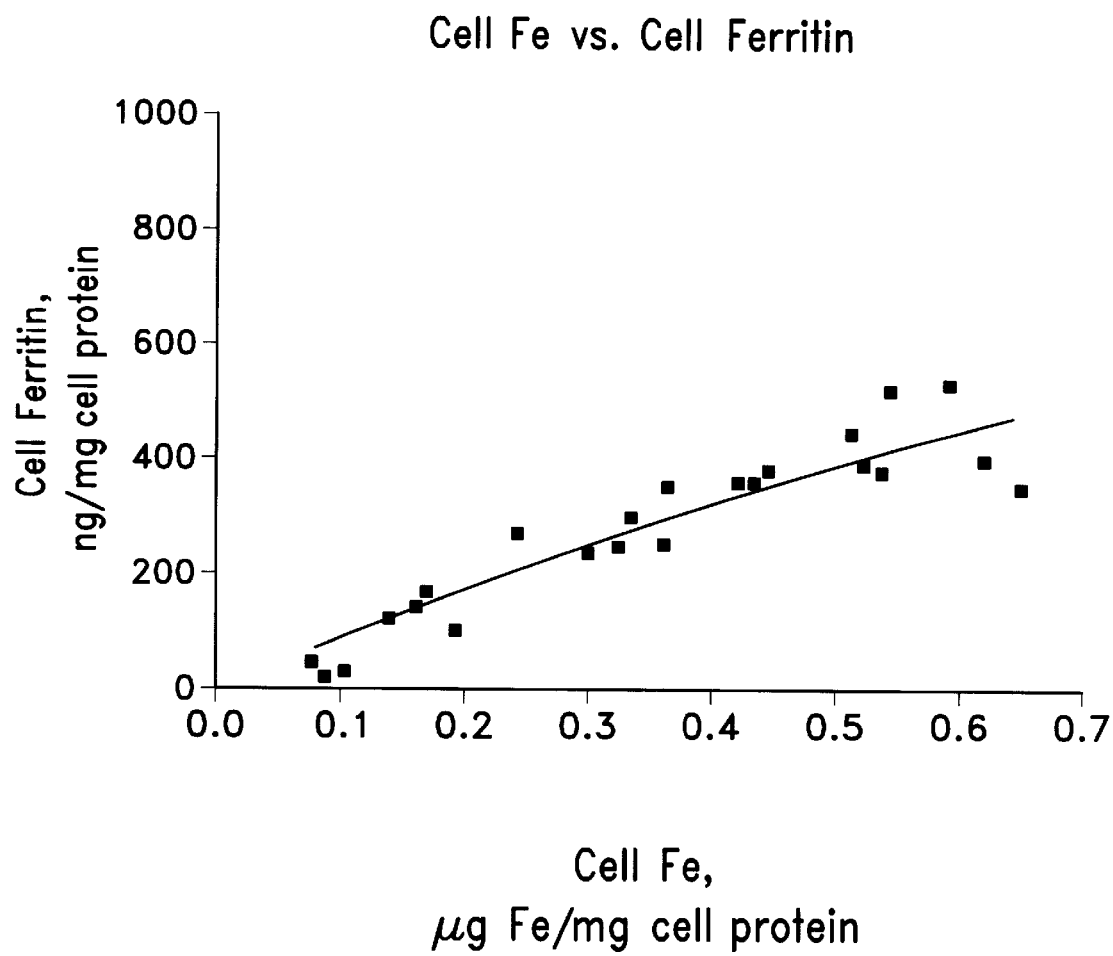

It should be noted that Caco-2 cell ferritin formation from cells exposed to digests containing $FeSO_4$ plus ascorbic acid was more than twice that observed for $FeSO_4$ combined with citric acid (FIGS. 2E and 3C).

Figure 4A:
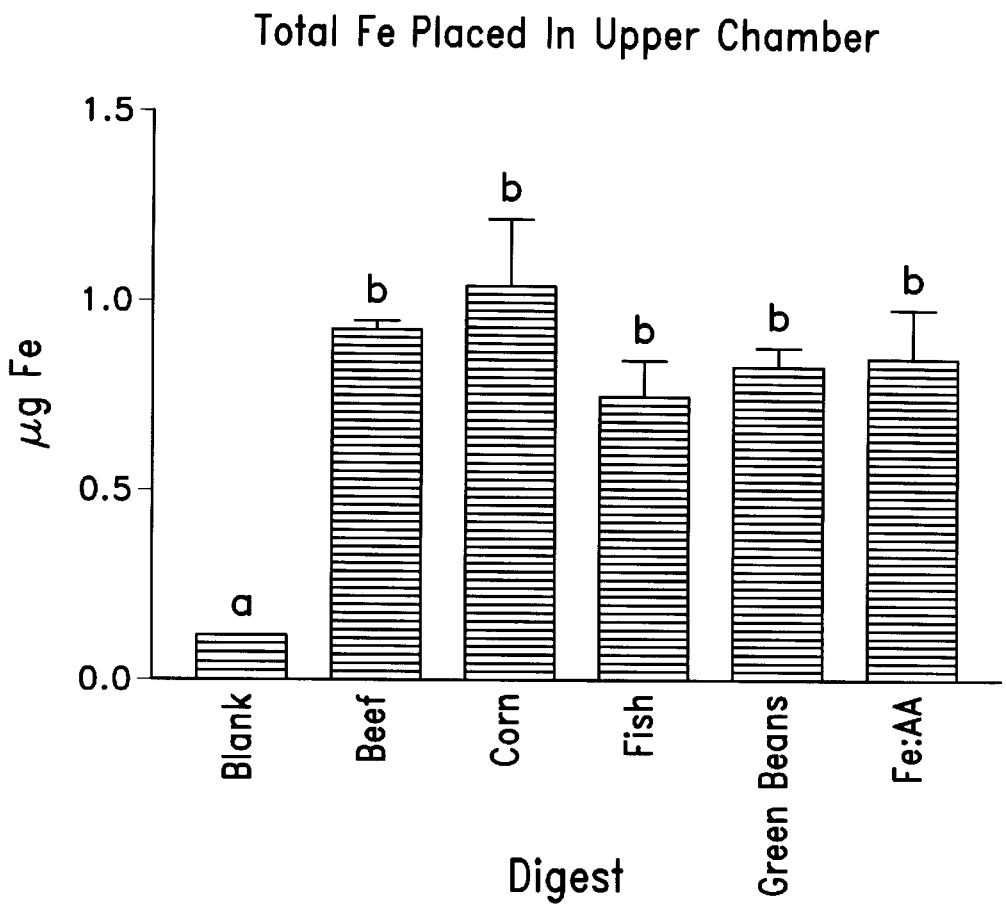
FIG. 4a–4d shows the measured variables for experiments comparing digests of beef, corn, fish and green beans. Digests were designed to include 10 $\mu$g Fe from each food. A digest containing 10 $\mu$g of Fe added as $FeSO_4$ and 1 mmol/L ascorbic acid (Fe:AA) was used as a positive control and reference standard. "Blank" indicates digest system components only (i.e. pepsin, pancreatin, bile extract), no added Fe or food. Bars (mean±SEM, n=5) with no letters in common are significantly different (P<0.05). Specific panels are defined as follows: (A) amount of Fe measured in 1.5 mL of digest placed in the upper chamber; (B) Caco-2 cell ferritin formation as measured 24 hr after the start of the intestinal digestion period; (C) Caco-2 cell ferritin formation as measured 24 hr after the start of the intestinal digestion period and expressed as a percentage of the Fe:AA control; (D) Caco-2 cell ferritin formation as measured 24 hr after the start of the intestinal digestion period and expressed per gram of food used in each digest.
Figure 4B:
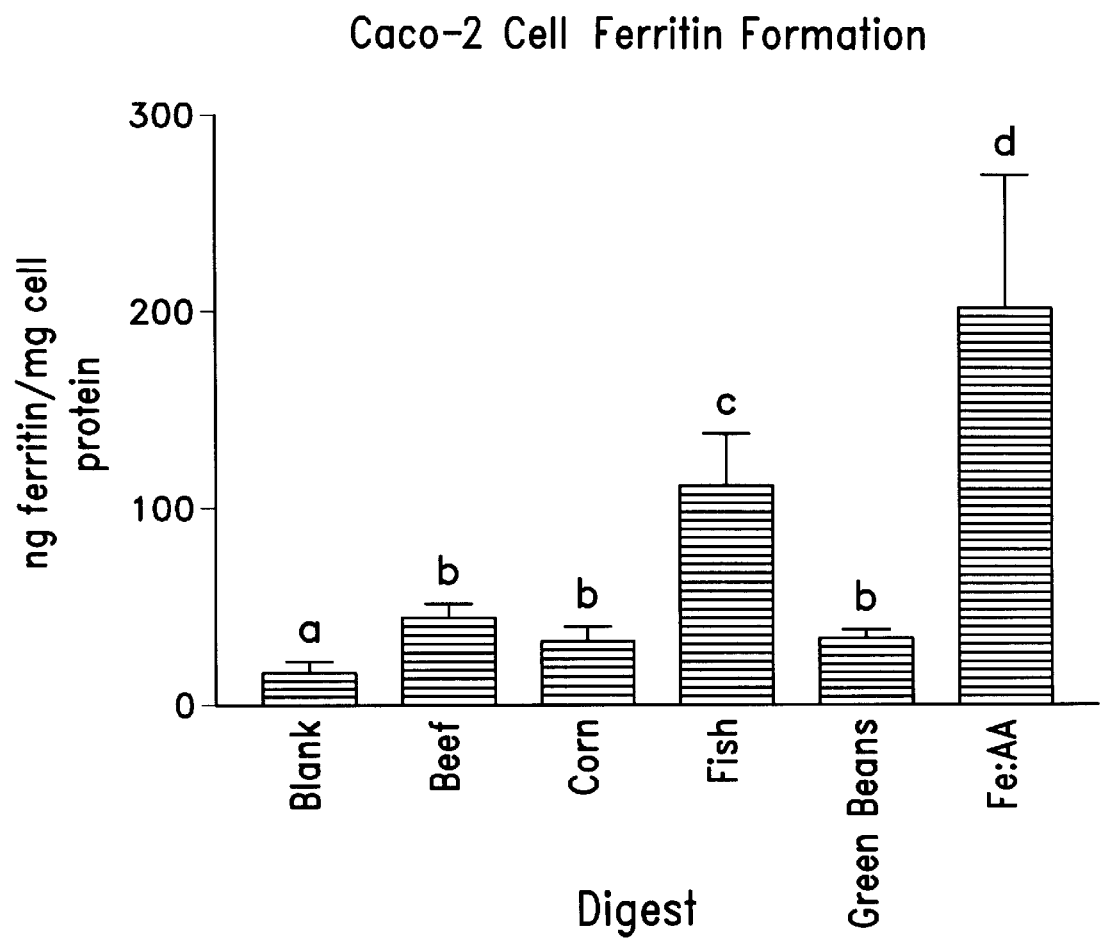
Figure 4C:
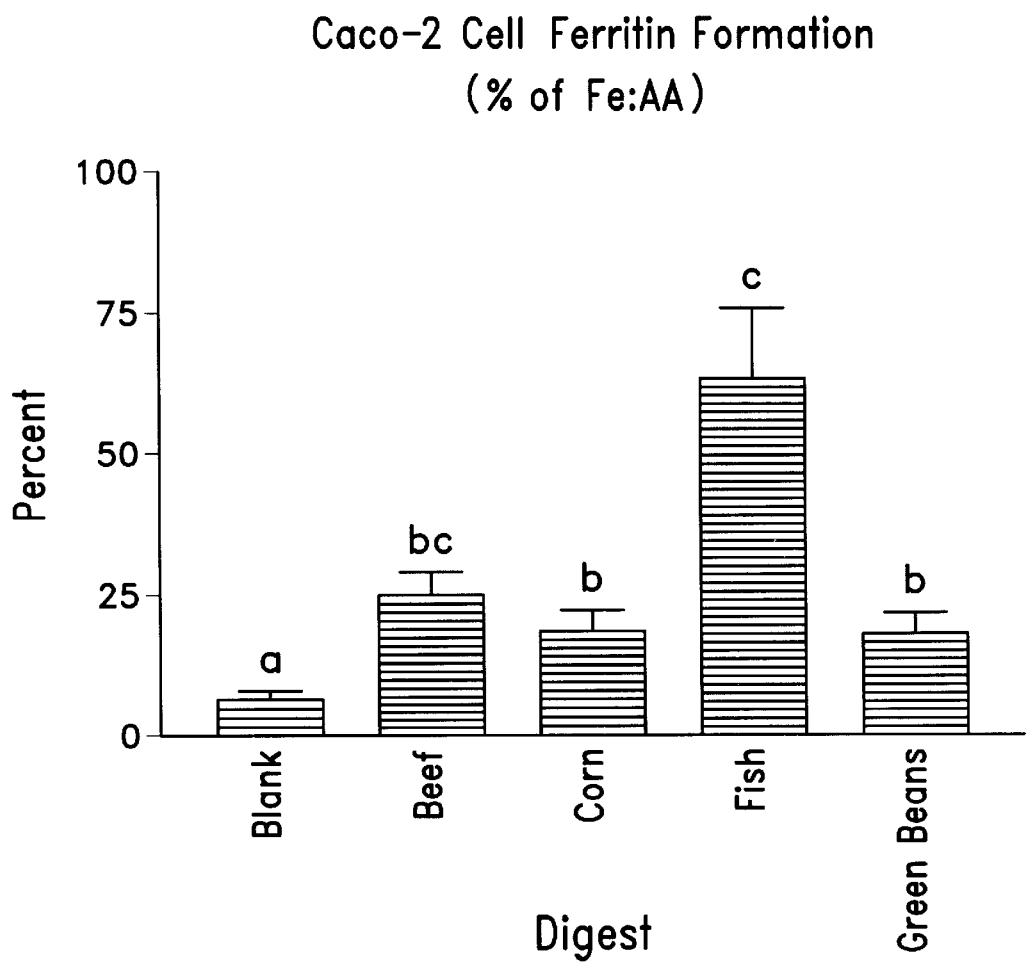
Figure 4D:
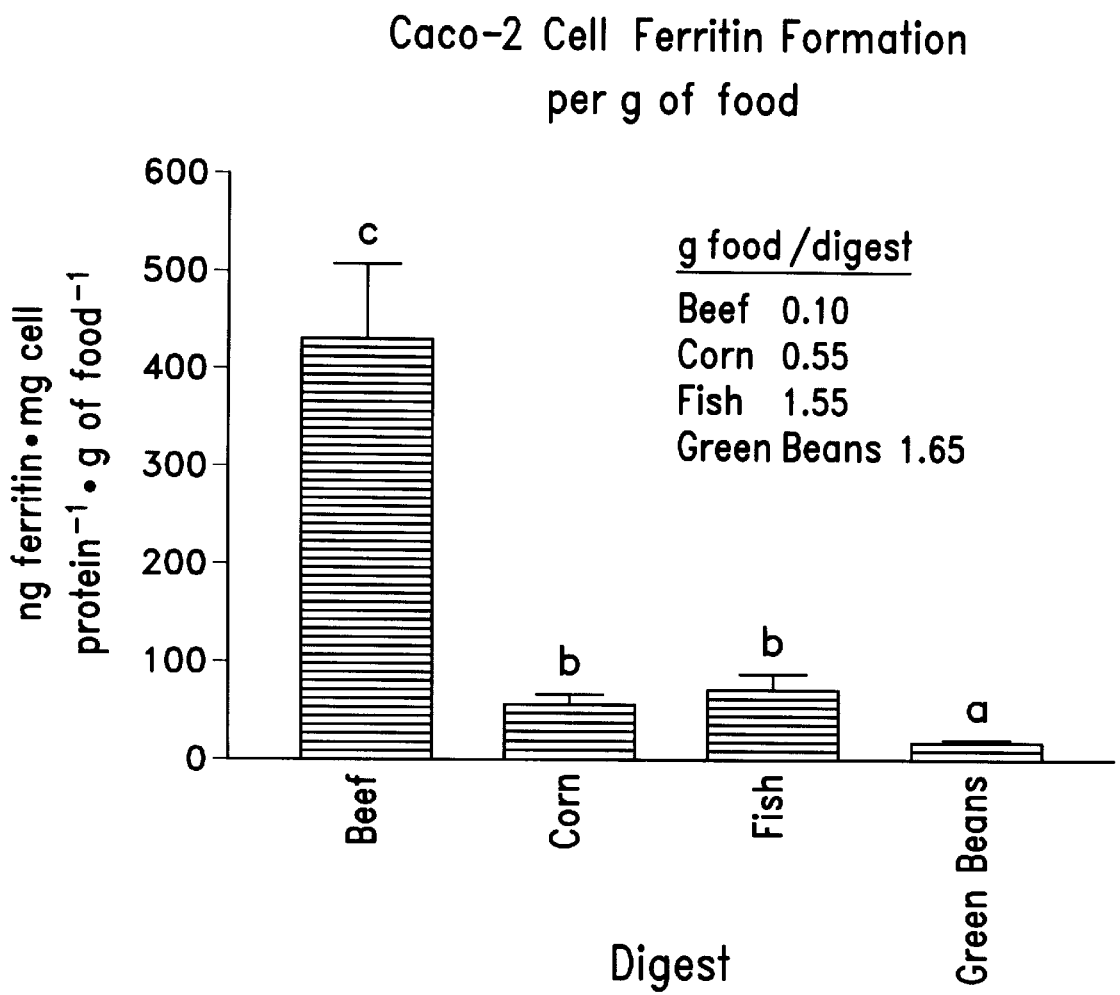

Experiments comparing samples of beef, corn, fish (haddock) and green beans were carried out. The beef and fish samples were from freeze-dried cooked samples containing 98.8 and 6.43 $\mu$g Fe/g sample, respectively (described previously in Glahn et al., 1996, supra). The corn sample was from a generic cornmeal purchased at a local market. It contained 18.1 $\mu$g Fe/g sample. The green bean sample was purchased at a local supermarket in pureed form as supplied by Gerber Products (Fremont, Mich.) as stage 1 food for infants. The green bean sample contained 6.08 $\mu$g Fe/g of sample. Digests of the above foods contained 10 $\mu$g Fe from each food. Comparisons of the Fe availability in the digests are summarized in FIG. 4. As a positive control and reference point, a digest of $FeSO_4$ in the presence of 1 mmol/L ascorbic acid was used in this series of experiments. For these experiments, an appropriate amount of each food was used, which resulted in a contribution of 10 $\mu$g Fe by the intrinsic Fe of the food. Thus, the amount of food used in each digest was as follows: beef, 0.10 g; corn, 0.55 g; fish, 1.55 g; and green beans, 1.65 g. FIG. 4A indicates that digest Fe concentrations were similar for all foods. Ferritin formation from digests containing fish was more than twice as much as that for beef, corn or green beans when expressed an ng ferritin/mg cell protein (FIG. 4B). Expressing ferritin formation as a percentage of the FeSO$_4$ plus ascorbic acid digest may also be useful and is shown in FIG. 4C. A significant difference between the beef and fish digests was not observed for this calculation as a result of the relatively high variability of the fish digest. Calculations of ferritin formation per gram of food are presented in FIG. 4D. Digests of beef yielded six to seven times the amount of ferritin formation per gram of food relative to the corn and fish digest, which were observed to be three to four times greater than the green bean digest.

The results of FIG. 4 further demonstrate the usefulness of ferritin formation as a measure of Fe availability. In these studies, it was expected that higher Fe availability would be evident from digests of beef and fish relative to corn and green beans if ferritin formation is to be a useful method for measuring Fe availability. To properly interpret these data, it is important to remember that these foods differed greatly in Fe content. Thus, different amounts of food were added to the digest to attain identical digest Fe concentrations (FIG. 4A). As shown in FIGS. 4B and C, the fish digest caused the greatest amount of ferritin formation relative to the beef, corn and green beans; however, on a per gram of food basis, the beef digest clearly induced the greatest amount of ferritin formation (FIG. 4D). In addition, the fish and green bean samples were very similar in Fe concentration, and the fish digest induced more ferritin formation than the green bean digest. From a nutritional standpoint, these results demonstrate greater Fe availability from animal tissue and thus support the use of ferritin formation as a measure of Fe uptake in this system.

An advantage of measurement of ferritin formation vs. quantification of radiolabeled Fe uptake is the issue of nonspecific binding of the radiolabeled Fe to the cell surface. In all Fe uptake studies, it is possible that some Fe from the uptake solution simply binds to the cell surface and is not truly taken up by the cell. Although methods exist to remove nonspecifically bound Fe from the Caco-2 cell surface, no studies have been conducted to determine if significant amounts of surface-bound Fe remain after such treatments (Glahn et al., 1995). Measurement of ferritin formation circumvents the issue of nonspecific binding because it is known to be a response to Fe internalized by the cell (Beard et al. 1996).

When utilizing ferritin formation as a method for measuring Fe uptake, the Fe content of the digestive enzymes must be as low as possible. For example, initial studies determined that commercially purchased pepsin contained 54 $\mu$g Fe/g pepsin. If untreated, a pepsin solution used in the model system would contribute enough Fe to the digest such that ferritin formation from a blank (no food or added Fe) digest containing ascorbic acid at 1 mmol/L would be four- to five-fold greater than that from a blank digest without ascorbic acid. Such an effect could significantly alter the accuracy and interpretation of data in this model system and thus negate the usefulness of this model for foods of low Fe concentration. As a result, both the pepsin and pancreatin-bile solutions were treated to remove Fe as described in Example 2. These methods were successful in removing >95% of the Fe from the pepsin solution, and >45% of the Fe from the pancreatin-bile solution. In spite of treatment of these solutions, a significant increase in ferritin formation was observed from cells exposed to a blank digest with 1 mmol/L ascorbic acid vs. cells exposed to a blank digest without ascorbic acid (FIG. 2E). However, the digest containing 10 $\mu$mol/L Fe with ascorbic acid exhibited approximately three times the amount of ferritin vs. the digest containing only ascorbic acid. These results demonstrate the sensitivity of this method and emphasize the importance of maintaining minimal Fe contamination in this system. Digest conditions that contain ample amounts of an iron uptake promoter can significantly increase the baseline measurement simply by acting on the contaminating iron present in the system.

Zn may interfere with Fe uptake (Wien et al. 1994. *J. Nutr. Biochem.* vol. 5, pp. 571–577), therefore the Zn concentration of the pepsin and pancreatin-bile solutions were also measured and found to be similar to values observed for Fe. Removal of Zn from the pepsin and pancreatin-bile mixture for the experimental procedures described was 99% and 64%, respectively. It is therefore recommended that commercial preparations of these enzymes be cleaned of Fe and Zn before use in this system. Concentrations of Fe and Zn at 0.07 mg/L are considered acceptable levels.

Contaminant Fe present in the system may also be introduced in the cell culture media (MEM) present on the cells during the intestinal digestion period. It is therefore important to use MEM with minimal Fe in its formulation. An acceptable level of Fe in MEM has been found to be $\leq 8$ $\mu$g/L.

The measurement of ferritin formation by Caco-2 cells is very sensitive. For example, measurement of ferritin formation from each culture well required only 10 $\mu$L from a total sample size of 2 mL. If needed, the ferritin assay could easily accommodate a sample size of 50 $\mu$L and possibly up to 100 $\mu$L. In addition, for the foods studied (FIG. 4), only 10 $\mu$g Fe was present in the digests and only 1 $\mu$g of that Fe was placed in the upper chamber of each culture well. Thus, the specific conditions such as digest tube size, Caco-2 cell monolayer size, incubation time and volume used in the upper chamber appear adequate and able to accommodate foods with relatively low Fe concentrations. This is an important feature because too much food may result in a pasty digest from which soluble Fe may not easily diffuse. It is also important to note that the foods studied here were very different (plant vs. animal tissue) and covered a broad range of Fe concentrations, thus demonstrating the versatility of this method. Although not particularly difficult, comparisons between plant and animal tissue are more complex because of the texture and overall difference between the foods. Particular care should thus be taken to achieve a representative sample when pipetting the digest into the upper chamber. The system is especially well-suited for comparisons of similar types of foods such as wheat and corn, or comparing several varieties of beans, pharmaceutical Fe supplements and foods such as infant formula and infant cereals.

The size (area) of the Caco-2 cell monolayer and the ability of the cell monolayer to take up nutrients are major factors in defining the specific conditions of the in vitro digestion. For example, in the examples presented herein, the cell monolayer of each well was cultured on an area of 9.4 cm$^2$, which resulted in ~2 mg of cell protein per well. The results presented in FIG. 2, which document one of the most available forms of Fe, indicate that maximal rate of Fe uptake occurred between 50 and 100 $\mu$mol/L Fe in the digest. Thus, an Fe concentration in the digest below 50 $\mu$mol/L is suggested in order to ensure maximum accuracy. An Fe concentration of 50 $\mu$mol/L in a 15 mL digest results in 41.9 $\mu$g Fe, which is sufficient to enable study of foods with high levels of Fe. Overall, the results demonstrate that the specific conditions used in this system allow for estimation of Fe availability from a diverse range of foods.

The following examples are intended only to further illustrate the invention and are not intended to limit the scope of the invention as defined by the claims.

EXAMPLES

Example 1

Preparation of Cell Culture

Caco-2 cells were obtained from the American Type Culture Collection (supra) at passage 17, and used in experiments at passage 25–33. Cells were seeded at a density of 50,000 cells/cm$^2$ in collagen-treated 6-well plates (6-well cell culture cluster disher, Costar, supra). The cells were grown in Dulbecco's modified Eagle's medium (GIBCO, supra) with 10% v/v fetal calf serum (GIBCO, supra), 25 mmol/L HEPES and 1% antibiotic antimycotic solution (GIBCO, supra). The cells were maintained at 37° C. in an incubator with a 5% CO$^2$/95% air atmosphere at constant humidity; the medium was changed every 2 d. The cells were used in the Fe uptake experiments at 13 d postseeding. Under these conditions, the amount of cell protein measured in each well was highly consistent from well to well within each culture plate.

Example 2

Preparation of Peptic and Intestinal Digests

Porcine pepsin (800–2500 units/mg protein), pancreatin (activity, 4×USP specifications) and bile extract (glycine and taurine conjugates of hyodeoxycholic and other bile salts) were purchased from Sigma Chemical Corp. (supra). Further preparation of the pepsin, pancreatin and bile extract was performed as follows. Shortly before use, 0.2 g pepsin was dissolved in 5 mL of 0.1 mol/L HCl, added to 2.5 g of Chelex-100 (Bio-Rad Laboratories, Hercules, Calif.) and shaken on a tabletop shaker for 30 min. The pepsin solution with Chelex was then poured into a 1.4-cm diameter filtration column to filter out the Chelex from the pepsin solution. An additional 5 mL of 0.1 mol/L HCl was added to the column and the filtrate collected into the pepsin solution. The final total volume of the eluted pepsin solution was 8 mL.

For the intestinal digestion, 0.05 g pancreatin and 0.3 g bile extract were dissolved in 25 ml of 0.1 mol/L NaHCO$_3$. Chelex-100 (12.5 g) was added and the resulting mixture was shaken for 30 min on a tabletop shaker. The mixture was then poured into a 1.6-cm diameter filtration column to filter out the Chelex. An additional 10 mL of 0.1 mol/L NaHCO$_3$ was added to the column and the filtrate collected into the pancreatin/bile solution. The final total volume of the pancreatin/bile solution was 27 mL. Treatment of the pepsin and pancreatin-bile solutions via the methods described above did not affect the activity of the enzymes.

Peptic and intestinal digestions were conducted on a rocking platform shaker (Reliable Scientific, supra) in an incubator at 37° C. with a 5% CO$_2$/95% air atmosphere maintained at constant humidity. The intestinal digestion was carried out in the upper chamber of a two-chamber system in 6-well plates, with the cell monolayer attached to the bottom surface of the lower chamber (FIG. 1).

To start the peptic digestion, the pH of each sample was adjusted to pH 2.0 with 5.0 mol/L HCl. The sample was transferred to a 50-mL screw-cap culture tube, and 0.5 mL of the pepsin solution was added per 10 mL of sample. The tube was capped, placed horizontally and incubated for 60 min on the rocking shaker at rocking speed #7 (55 oscillations/min). For the intestinal digestion step, the pH of the sample (or digest) was raised to pH 6 by dropwise addition of 1 mol/L NaHCO$_3$. Then 2.5 mL of pancreatin-bile extract mixture was added per 10 mL of original sample. The pH was adjusted to pH 7 with NaOH, and the volume was brought to 15 mL with 120 mmol/L NaCl and 5 mmol/L KCl

Example 3

Preparation of Insert for Formation of Upper Chamber

The insert is formed by fitting a Transwell insert ring (Costar, supra) with a 15,000 molecular weight cut-off dialysis membrane (Spectra/Por 2.1, Spectrum Medical, supra). The insert ring is sized to fit a well of the 6-well culture plate described in Example 1. The membranes were soaked in deionized water before use. The dialysis membrane was held in place with a silicone ring (Web Seal, supra). After the dialysis membrane was fastened to the insert ring, the entire unit was sterilized in 70% ethanol and kept in sterile water until use.

Example 4

Preparation of Cell Monolayer

Immediately before the intestinal digestion period, the growth medium was removed from each culture well, and the cell layer was washed twice with 37° C. Minimum Essential Medium (MEM, GIBCO, supra) at pH 7. This MEM was chosen because it contained no added Fe; upon formulation with the following ingredients, it was always found to contain <8 $\mu$g Fe/L. The MEM was supplemented with 10 mmol/L PIPES (piperazine-N,N'-bis-[2-ethanesulfonic acid]), 1% antibiotic-antimycotic solution (Sigma, supra), hydrocortisone (4 mg/L), insulin (5 mg/L), selenium (5 $\mu$g/L), triiodothyronine (34 $\mu$g/L) and epidermal growth factor (20 $\mu$g/L). A fresh 1.0-mL aliquot of MEM covered the cells during the experiment. A sterilized insert ring described in Example 3 was inserted into the well, creating the two-chamber system. A 1.5 mL aliquot of the intestinal digest was pipetted into the upper chamber. The plate was covered and incubated on the rocking shaker at 6 oscillations/min for 2 hr.

When the intestinal digestion was terminated, the insert ring and digest were removed. The solution in the bottom chamber was allowed to remain on the cell monolayer and an additional 1 mL of MEM was added to each well. The cell culture plate was then returned to the incubator for an additional 22 hr, after which the cells were harvested for analysis.

Example 5

Harvesting of Cell Monolayer for Analysis of Ferritin and Cell-Associated Fe Exactly 24 hr after the start of the intestinal digestion period, the cell monolayers were harvested for various analyses. To harvest the cells, the medium covering the cells was removed and the cells washed once with a 2-mL volume of a rinse solution containing 140 mmol/L NaCl, 5 mmol/L KCl and 10 mmol PIPES, at pH 7. The rinse solution was then aspirated and a 2-mL volume of a freshly prepared removal solution was placed on the cell monolayer for 10 min. The removal solution consisted of the above rinse solution with an additional 5 mmol/L sodium hydrosulfite and 1 mmol/L bathophenananthrolene disulfonic acid (BPDS).

After the removal period the removal solution was aspirated and the cell monolayer washed with a 2-mL volume of rinse solution. The rinse solution was then aspirated, and 2 mL of deionized water was placed on each monolayer. The plates were then placed on a rack such that the bottom of each plate was in contact with the water of a benchtop sonicator, which was kept in a cold room at 4° C. The cells were sonicated for 15 min, scraped from the plate surface, harvested along with the 2-mL volume of water in each well and then stored at −20° C.

Example 6

Analyses

All glassware used in the sample preparation and analyses was acid-washed. Caco-2 cell protein was measured on samples that had been solubilized on 0.5 mol/L NaOH, using a semimicro adaptation of the Bio-Rad DC protein assay kit (Bio-Rad Laboratories, supra). A one-stage, two-site immunoradiometric assay was used to measure Caco-2 cell ferritin content (PER-IRON II Ferritin Assay, RAMCO Laboratories, Houston, Tex.). A 10-$\mu$L sample of the sonicated Caco-2 cell monolayer, harvested in 2 mL of water, was used for each ferritin measurement.

Analyses of the iron content of the experimental solutions, foods, digests and Caco-2 cell monolayers were conducted by using an inductively coupled plasma emission spectrometer (ICAP Model 61E Trace Analyzer, Thermo Jarrell Ash Corporation, Franklin, Mass.).

Experiments were replicated four to five times for each experimental protocol. Each experimental treatment was performed in duplicate for each replication of the experiment. The duplicates were averaged, and this average value was the data point used in the statistical analysis. The position of each experimental treatment in the multiwell plate was different for each replication of the experiment. Replicates of each experiment were conducted on separate days. The exact number of replicates is noted in the description of the figure.

Statistical analysis of the data was performed using the software package GraphPad Prism (GraphPad Software, San Diego, Calif.). Statistical analyses were conducted according to the methods of Motulsky (1995). Before analysis, data were log transformed to achieve equal variance. Because each replication of an experiment in the study was a paired comparison, a repeated measures ANOVA was performed with Tukey's post-hoc test to compare the various means of each series of experiments. Means were considered significantly different if P-values were $\leq 0.05$.

For each experiment, two 6-well plates without Caco-2 cells were included. These plates were treated identically to those with cells. These plates served to determine the amount of iron that diffused into the bottom chamber under the experimental conditions defined herein. Because a large portion of the Fe that passes into the bottom chamber may be taken up by the cells, these plates were used for more accurate measurement of the amount of dialyzable Fe. It was found that virtually all of the Fe that passed into the bottom chamber of this model system was soluble.

I claim:

1. A method of predicting Fe availability in a food sample, said method comprising
   a) preparing a culture of intestinal epithelial cells;
   b) preparing an insert comprising a dialysis membrane capable of allowing diffusion of Fe from a digest of said food sample across the membrane and simultaneously protecting cells from digestive enzymes and microbial contamination present in said digest;
   c) preparing a peptic digest of said food sample, followed by an intestinal digest;
   d) preparing a monolayer of the intestinal epithelial cells of step a) in Fe-free culture medium in a chamber;
   e) fitting the insert of step b) into the chamber of step d) such that the membrane is secured with a liquid tight seal, resulting in a two-chamber system having a lower chamber with a cell monolayer attached to the bottom surface and an upper chamber formed by the membrane, with the membrane in fluid contact with the culture medium;
   f) adding an aliquot of the intestinal digest of step c) to the upper chamber and incubating the digest for a predetermined time, allowing diffusion of Fe-containing fluid into the lower chamber as digestion occurs;
   g) removing the insert containing the intestinal digest;
   h) adding additional Fe-free medium to the lower chamber containing the cell monolayer;
   i) incubating the cells for a period of time sufficient for ferritin formation to occur; and
   j) harvesting the cells and measuring the amount of ferritin formed.

2. The method of claim 1, wherein said intestinal epithelial cells are human intestinal epithelial cells.

3. The method of claim 2, wherein said human intestinal epithelial cells are Caco-2 cells.

* * * * *